(12) United States Patent
Mower (10) Patent No.: US 8,447,399 B2
(45) Date of Patent: *May 21, 2013

(54) SYSTEM AND METHOD FOR MANAGING DETRIMENTAL CARDIAC REMODELING

(75) Inventor: Morton M. Mower, Baltimore, MD (US)

(73) Assignee: MR3 Medical, LLC, North Oaks, MN (US)

( * ) Notice: Subject to any disclaimer, the term of this patent is extended or adjusted under 35 U.S.C. 154(b) by 1450 days.

This patent is subject to a terminal disclaimer.

(21) Appl. No.: 12/060,334

(22) Filed: Apr. 1, 2008

(65) Prior Publication Data

US 2008/0287855 A1    Nov. 20, 2008

Related U.S. Application Data (63) Continuation of application No. 11/141,403, filed on May 31, 2005, now Pat. No. 7,440,800, which is a continuation-in-part of application No. 10/053,750, filed on Jan. 21, 2002, now Pat. No. 8,290,585, which is a continuation of application No. 09/690,947, filed on Oct. 18, 2000, now Pat. No. 6,341,235, which is a continuation-in-part of application No. 09/008,636, filed on Jan. 16, 1998, now Pat. No. 6,136,019, which is a continuation-in-part of application No. 08/699,552, filed on Aug. 19, 1996, now Pat. No. 5,871,506.

(60) Provisional application No. 60/575,121, filed on May 28, 2004.

(51) Int. Cl.
*A61N 1/00* (2006.01)

(52) U.S. Cl.
USPC .................................................... 607/9

(58) Field of Classification Search
USPC ..................................................... 607/4–28
See application file for complete search history.

(56) References Cited

U.S. PATENT DOCUMENTS

| 3,924,641 A | 12/1975 | Weiss |
| 3,946,745 A | 3/1976 | Siang-Lai et al. |
| 4,010,758 A | 3/1977 | Rockland et al. |

(Continued)

FOREIGN PATENT DOCUMENTS

| AU | 2003267188 A1 | 4/2004 |
| EP | 0491649 B1 | 9/1996 |

(Continued)

OTHER PUBLICATIONS

Cleland, Brian G. "A Conceptual Basis for Pacing Waveforms," Pace, vol. 19, 1177-1185 (Aug. 1996).

(Continued)

*Primary Examiner* — Scott Getzow
(74) *Attorney, Agent, or Firm* — The Marbury Law Group, PLLC (57) ABSTRACT

A system and method for managing and inhibiting cardiac remodeling in MI patients. Bi-ventricular stimulation is constantly provided with and without sensing to encourage normal pumping of the heart on a consistent basis. Pulses are administered using an anodal pulse followed by a cathodal pulse to stimulate cardiac muscle contraction. Stem cells are administered to MI areas to encourage regeneration of cardiac tissue in the damaged area. Stimulation may be provided to both healthy and compromised cardiac tissue.

21 Claims, 3 Drawing Sheets

U.S. PATENT DOCUMENTS

| | | |
|---|---|---|
| 4,019,519 A | 4/1977 | Geerling |
| 4,055,190 A | 10/1977 | Tany |
| 4,222,386 A | 9/1980 | Smolnikov et al. |
| 4,233,986 A | 11/1980 | Tannenbaum |
| 4,298,007 A | 11/1981 | Wright et al. |
| 4,327,322 A | 4/1982 | Yukl |
| 4,343,312 A | 8/1982 | Cals et al. |
| 4,392,496 A | 7/1983 | Stanton |
| 4,402,322 A | 9/1983 | Duggan |
| 4,429,697 A | 2/1984 | Nappholz et al. |
| 4,444,195 A | 4/1984 | Gold |
| 4,456,012 A | 6/1984 | Lattin |
| 4,481,953 A | 11/1984 | Gold et al. |
| 4,498,478 A | 2/1985 | Bourgeois |
| 4,503,857 A | 3/1985 | Boute et al. |
| 4,539,991 A | 9/1985 | Boute et al. |
| 4,543,956 A | 10/1985 | Herscovici |
| 4,545,956 A | 10/1985 | Ciszewski et al. |
| 4,569,350 A | 2/1986 | Mumford et al. |
| RE32,091 E | 3/1986 | Stanton |
| 4,612,934 A | 9/1986 | Borkan |
| 4,637,397 A | 1/1987 | Jones et al. |
| 4,646,744 A | 3/1987 | Capel |
| 4,662,377 A | 5/1987 | Heilman et al. |
| 4,723,552 A | 2/1988 | Kenyon et al. |
| 4,729,376 A | 3/1988 | DeCote, Jr. |
| 4,754,759 A | 7/1988 | Allocca |
| 4,781,194 A | 11/1988 | Elmqvist |
| 4,821,724 A | 4/1989 | Whigham et al. |
| 4,823,810 A | 4/1989 | Dervieux |
| 4,875,484 A | 10/1989 | Anzai et al. |
| 4,903,700 A | 2/1990 | Whigham et al. |
| 4,919,140 A | 4/1990 | Borgens et al. |
| 4,924,880 A | 5/1990 | O'Neill et al. |
| 4,940,054 A | 7/1990 | Grevis et al. |
| 4,944,298 A | 7/1990 | Sholder |
| 4,976,264 A | 12/1990 | Petrofsky |
| 4,989,605 A | 2/1991 | Rossen |
| 4,996,987 A | 3/1991 | Petrofsky |
| 5,018,522 A | 5/1991 | Mehra |
| 5,027,815 A | 7/1991 | Funke et al. |
| 5,036,850 A | 8/1991 | Owens |
| 5,048,522 A | 9/1991 | Petrofsky |
| 5,052,391 A | 10/1991 | Silberstone et al. |
| 5,058,584 A | 10/1991 | Bourgeois |
| 5,063,929 A | 11/1991 | Bartelt et al. |
| 5,065,083 A | 11/1991 | Owens |
| 5,069,211 A | 12/1991 | Bartelt et al. |
| 5,083,564 A | 1/1992 | Scherlag |
| 5,097,833 A | 3/1992 | Campos |
| 5,105,810 A | 4/1992 | Collins et al. |
| 5,109,847 A | 5/1992 | Liss et al. |
| 5,111,811 A | 5/1992 | Smits |
| 5,117,826 A | 6/1992 | Bartelt et al. |
| 5,156,147 A | 10/1992 | Warren et al. |
| 5,163,429 A | 11/1992 | Cohen |
| 5,181,511 A | 1/1993 | Nickolls et al. |
| 5,193,535 A | 3/1993 | Bardy et al. |
| 5,205,284 A | 4/1993 | Freeman |
| 5,209,229 A | 5/1993 | Gilli |
| 5,213,098 A | 5/1993 | Bennett et al. |
| 5,215,083 A | 6/1993 | Drane et al. |
| 5,224,475 A | 7/1993 | Berg et al. |
| 5,224,476 A | 7/1993 | Ideker et al. |
| 5,233,985 A | 8/1993 | Hudrlik |
| 5,292,340 A | 3/1994 | Crosby et al. |
| 5,300,096 A | 4/1994 | Hall et al. |
| 5,314,423 A | 5/1994 | Seney |
| 5,314,495 A | 5/1994 | Kovacs |
| 5,318,591 A | 6/1994 | Causey, III et al. |
| 5,332,401 A | 7/1994 | Davey et al. |
| 5,334,220 A | 8/1994 | Sholder |
| 5,340,361 A | 8/1994 | Sholder |
| 5,350,401 A | 9/1994 | Levine |
| 5,391,185 A | 2/1995 | Kroll |
| 5,411,525 A | 5/1995 | Swanson et al. |
| 5,411,547 A | 5/1995 | Causey, III |
| 5,417,718 A | 5/1995 | Kleks et al. |
| 5,421,830 A | 6/1995 | Epstein et al. |
| 5,422,525 A | 6/1995 | Mansir |
| 5,423,868 A | 6/1995 | Nappholz et al. |
| 5,441,522 A | 8/1995 | Schuller |
| 5,458,619 A | 10/1995 | Olson |
| 5,458,625 A | 10/1995 | Kendall |
| 5,468,254 A | 11/1995 | Hahn et al. |
| 5,480,413 A | 1/1996 | Greenhut et al. |
| 5,487,759 A | 1/1996 | Bastyr et al. |
| 5,507,781 A | 4/1996 | Kroll et al. |
| 5,514,161 A | 5/1996 | Limousin |
| 5,514,162 A | 5/1996 | Bornzin et al. |
| 5,514,163 A | 5/1996 | Markowitz et al. |
| 5,522,858 A | 6/1996 | van der Veen |
| 5,527,347 A | 6/1996 | Shelton et al. |
| 5,534,015 A | 7/1996 | Kroll et al. |
| 5,534,018 A | 7/1996 | Wahlstrand et al. |
| 5,540,730 A | 7/1996 | Terry, Jr. et al. |
| 5,545,186 A | 8/1996 | Olson et al. |
| 5,549,652 A | 8/1996 | McClure et al. |
| 5,562,708 A | 10/1996 | Combs et al. |
| 5,571,143 A | 11/1996 | Hoegnelid et al. |
| 5,584,868 A | 12/1996 | Salo et al. |
| 5,601,608 A | 2/1997 | Mouchawar |
| 5,601,611 A | 2/1997 | Fayram et al. |
| 5,601,615 A | 2/1997 | Markowitz et al. |
| 5,620,470 A | 4/1997 | Gliner et al. |
| 5,620,471 A | 4/1997 | Duncan |
| 5,626,620 A | 5/1997 | Kieval et al. |
| 5,649,966 A | 7/1997 | Noren et al. |
| 5,651,378 A | 7/1997 | Matheny et al. |
| 5,658,319 A | 8/1997 | Kroll |
| 5,662,698 A | 9/1997 | Altman et al. |
| 5,674,253 A | 10/1997 | Adams et al. |
| 5,683,431 A | 11/1997 | Wang |
| 5,690,691 A | 11/1997 | Chen et al. |
| 5,697,953 A | 12/1997 | Kroll et al. |
| 5,713,924 A | 2/1998 | Min et al. |
| 5,713,929 A | 2/1998 | Hess et al. |
| 5,718,720 A | 2/1998 | Prutchi et al. |
| 5,735,876 A | 4/1998 | Kroll et al. |
| 5,735,879 A | 4/1998 | Gliner et al. |
| 5,741,303 A | 4/1998 | Kroll et al. |
| 5,800,464 A | 9/1998 | Kieval |
| 5,800,465 A | 9/1998 | Thompson et al. |
| 5,814,079 A | 9/1998 | Kieval |
| 5,836,994 A | 11/1998 | Bourgeois |
| 5,855,592 A | 1/1999 | McGee et al. |
| 5,855,594 A | 1/1999 | Olive et al. |
| 5,871,506 A | 2/1999 | Mower |
| 5,871,560 A | 2/1999 | Fluch et al. |
| 5,876,422 A | 3/1999 | van Groeningen |
| 5,968,081 A | 10/1999 | Levine |
| 6,026,326 A | 2/2000 | Bardy |
| 6,067,470 A | 5/2000 | Mower |
| 6,136,019 A | 10/2000 | Mower |
| 6,141,586 A | 10/2000 | Mower |
| 6,141,587 A | 10/2000 | Mower |
| 6,151,525 A | 11/2000 | Soykan et al. |
| 6,178,351 B1 | 1/2001 | Mower |
| 6,216,039 B1 | 4/2001 | Bourgeois |
| 6,223,072 B1 | 4/2001 | Mika et al. |
| 6,248,126 B1 | 6/2001 | Lesser et al. |
| 6,263,242 B1 | 7/2001 | Mika et al. |
| 6,292,693 B1 | 9/2001 | Darvish et al. |
| 6,317,631 B1 | 11/2001 | Ben-Haim et al. |
| 6,360,126 B1 | 3/2002 | Mika et al. |
| 6,363,279 B1 | 3/2002 | Ben-Haim et al. |
| 6,370,430 B1 | 4/2002 | Mika et al. |
| 6,411,845 B1 | 6/2002 | Mower |
| 6,424,866 B2 | 7/2002 | Mika et al. |
| 6,571,127 B1 | 5/2003 | Ben-Haim et al. |
| 6,597,952 B1 | 7/2003 | Mika et al. |
| 6,628,988 B2 * | 9/2003 | Kramer et al. ............ 607/9 |
| 6,775,574 B1 | 8/2004 | Soykan et al. |
| 6,947,792 B2 | 9/2005 | Ben-Haim et al. |
| 2002/0124855 A1 | 9/2002 | Chachques |
| 2002/0161410 A1 | 10/2002 | Kramer et al. |
| 2003/0014097 A1 | 1/2003 | Putz et al. |

| | | | |
|---|---|---|---|
| 2004/0049236 A1 | 3/2004 | Kramer et al. | |
| 2004/0054381 A1 | 3/2004 | Pastore et al. | |
| 2004/0158289 A1 | 8/2004 | Girouard et al. | |
| 2005/0002912 A1 | 1/2005 | Chachques | |

FOREIGN PATENT DOCUMENTS

| | | |
|---|---|---|
| EP | 0600631 B1 | 12/1999 |
| EP | 0850662 B1 | 6/2003 |
| EP | 1381426 A1 | 1/2004 |
| EP | 1536859 A1 | 6/2005 |
| EP | 0870516 B1 | 11/2005 |
| EP | 0813889 B1 | 5/2009 |
| FR | 2763247 A1 | 11/1998 |
| JP | 2005538776 T | 12/2005 |
| WO | WO 93/01861 A1 | 2/1993 |
| WO | WO 97/13547 A1 | 4/1997 |
| WO | WO 97/25098 A1 | 7/1997 |
| WO | WO 99/36124 A1 | 7/1999 |
| WO | WO 99/61101 A1 | 12/1999 |
| WO | WO 00/01443 A1 | 1/2000 |
| WO | WO 02/087694 A1 | 11/2002 |
| WO | WO 2004/024229 A1 | 3/2004 |

OTHER PUBLICATIONS

Estes et al., Implantable Cardioverter-Defibrillators, p. 181 (1994).

Euler De, Scanlon PJ. "Acetylcholine Release by a Stimulus Train Lowers Atrial Fibrillation Threshold," AM J Physiol. Oct. 1987;253(4 pt 2):H863-8.

Greenspan, Allen M., M.D., "Electrophysiology of Pacing," 29-35, Ideal Cardiac Pacing, vol. 37 in the Series, Major Problems in Clinical Surgery (1984).

Guyton, Textbook of Medical Physiology, 8th Edition, Chapter 9, pp. 98-99, 1991.

Hoffman, Brian F., M.D., and Paul F. Cranefield, M.D., Electrophysiology of the Heart, 220-222, (1976).

Khaykin, Yaariv; Saad, Eduardo B.; Wilkoff, Bruce L. "Pacing in heart failure: The benefit of resynchronization." Cleveland Clinic Journal of Medicine, Oct. 2003, pp. 841-865, vol. 70 No. 10.

Lorente P, Delgado C, Delmar M, Henzel D, Jalife J., "Hysteresis in the Excitability of Isolated Guinea Pig Ventricular Myocytes," Circ Res. Nov. 1991;69(5):1301-15.

Roth, Bradley J., Ph.D., "Strength-Internal Curves for Cardiac Tissue Predicted Using the Bidomain Model," Journal of Cardiovascular Electrophysiology, vol. 7, No. 8, 722-737 (Aug. 1996).

Siddons, Harold and Sowton, Edgar, "Cardiac Pacemakers," 152-154. (1967).

Stix, Guenter, et al. "Chronic electrical stimulation during the absolute refractory period of the myocardium improves severe heart failure." European Heart Journal (2004) 25, 650-655 (Elsevier Ltd. on behalf of European Society of Cardiology).

Willems, Rik; SIPIDO, Karin R. "Nonexcitatory stimulation as a novel treatment for heart failure: cause for excitement?" European Heart Journal (2004) 25, 626-628 (Elsevier Ltd. on behalf of European Society of Cardiology).

Zilberter Yi, Starmer CF, Grant AO. "Open Na+ Channel Blockade: Multiple Rest States Revealed by Channel Interactions with Disopyramide and Quinidine, " Am J Physiol. May 1994;266(5 pt 2):H2007-17.

* cited by examiner

SYSTEM AND METHOD FOR MANAGING DETRIMENTAL CARDIAC REMODELING

CROSS REFERENCE TO RELATED APPLICATIONS

This application is a continuation of U.S. patent application Ser. No. 11/141,403 filed May 31, 2005 now U.S. Pat. No. 7,440,800, which is a continuation-in-part of U.S. patent application Ser. No. 10/053,750 filed Jan. 21, 2002 now U.S. Pat. No. 8,290,585, which is a continuation of U.S. patent application Ser. No. 09/690,947, filed Oct. 18, 2000, now U.S. Pat. No. 6,341,235, which is a continuation-in-part of U.S. patent application Ser. No. 09/008,636 filed Jan. 16, 1998, now U.S. Pat. No. 6,136,019, which is a continuation-in-part of U.S. patent application Ser. No. 08/699,552, filed Aug. 19, 1996, now U.S. Pat. No. 5,871,506. The Ser. Nos. 10/053,750, 09/690,947, 09/008,636, and 08/699,552 applications are all incorporated by reference herein, in their entirety, for all purposes. The Ser. No. 11/141,403 application claims priority under 35 U.S.C. §119(e) from provisional application No. 60/575,121 filed May 28, 2004. The 60/575,121 provisional application is also incorporated by reference herein, in its entirety, for all purposes.

BACKGROUND

This application is generally related to treatment of the heart, and more particularly to managing and preventing detrimental cardiac remodeling following myocardial infarction. Remodeling of the heart is a harmful physical change in the heart that occurs with heart failure, heart attack, and heart disease. Remodeling is characterized by enlargement of the heart and thinning of the heart walls. For example, after a heart attack, while the normal heart muscle responds normally to excitatory pulses, tissue that is damaged by the heart attack does not respond or responds in a slower than normal rate to excitatory pulses. The healthy tissue however, continuing to function normally, places increased stress on the damaged and marginalized tissue, thereby "stretching" it. The stretching increases the volume of blood held by the heart resulting in a short term increased blood output via a Frank-Sterling mechanism. In this way, the heart muscle behaves something like a rubber band—the more it is stretched, the more "snap" the heart generates. However, if cardiac muscle is overstretched, or if the heart is stretched repetitively over a long period of time, it eventually loses its "snap" and becomes flaccid (a form of remodeling). Remodeling progresses in stages. Following a heart attack or as a consequence of heart disease, the heart becomes rounder and larger. Heart muscle cells die and the heart as a pump gets weaker. If the remodeling is allowed to progress, the heart's main pumping chamber—the left ventricle—enlarges and changes shape, getting rounder. The heart also undergoes changes at the cell level.

The heart is divided into the right side and the left side. The right side, comprising the right atrium and ventricle, collects and pumps de-oxygenated blood to the lungs to pick up oxygen. The left side, comprising the left atrium and ventricle, collects and pumps oxygenated blood to the body. Oxygen-poor blood returning from the body enters the right atrium through the vena cava. The right atrium contracts, pushing blood through the tricuspid valve and into the right ventricle. The right ventricle contracts to pump blood through the pulmonic valve and into the pulmonary artery, which connects to the lungs. The blood picks up oxygen in the lungs and then travels back to the heart through the pulmonary veins. The pulmonary veins empty into the left atrium, which contracts to push oxygenated blood into the left ventricle. The left ventricle contracts, pushing the blood through the aortic valve and into the aorta, which connects to the rest of the body. Coronary arteries extending from the aorta provide the heart blood.

The heart's own pacemaker is located in the atrium and is responsible for initiation of the heartbeat. The heartbeat begins with activation of atrial tissue in the pacemaker region (i.e., the sinoatrial or "SA" node), followed by cell-to-cell spread of excitation throughout the atrium. The only normal link of excitable tissue connecting the atria to the ventricles is the atrioventricular (AV) node located at the boundary between the atria and the ventricles. Propagation takes place at a slow velocity, but at the ventricular end the bundle of His (i.e., the electrical conduction pathway located in the ventricular septum) and the bundle braides carry the excitation to many sites in the right and left ventricle at a relatively high velocity of 1-2 m/s. The slow conduction in the AV junction results in a delay of around 0.1 seconds between atrial and ventricular excitation. This timing facilitates terminal filling of the ventricles from atrial contraction prior to ventricular contraction. After the slowing of the AV node, the bundle of His separates into two bundle branches (left and right) propagating along each side of the septum. The bundles ramify into Purkinje fibers that diverge to the inner sides of the ventricular walls. This insures the propagation of excitatory pulses within the ventricular conduction system proceeds at a relative high speed when compared to the propagation through the AV node.

The syndrome of "heart failure" is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. Typically, the elevated filling pressures result in dilatation of the left ventricular chamber. Etiologies that can lead to this form of failure include idiopathic cardiomyopathy, viral cardiomyopathy, and ischemic cardiomyopathy.

Heart failure is a chronic condition that affects over five million Americans, and is the most common reason for hospitalization among elderly persons. Contrary to its name, heart failure is not a heart attack. Neither does the heart suddenly stop beating. Heart failure means that the heart is failing to pump enough blood to meet the body's needs. It often occurs in patients whose hearts have been weakened or damaged by a heart attack or other conditions. As the heart continues to fail, patients may experience breathlessness, fluid build-up in the limbs and severe fatigue. Delays in response of the septum to excitatory pulse may cause contractions that are not simultaneous and therefore the ventricular contraction pattern is non-concentric. In this mode, the heart is beating inefficiently.

When the heart is working properly, both of its lower chambers (ventricles) pump at the same time and in sync with the pumping of the two upper chambers (atria). Up to 40 percent of heart failure patients, however, have disturbances in the conduction of electrical impulses to the ventricles (e.g., bundle branch block or intraventricular conduction delay). As a result, the left and right ventricles are activated at different times. When this happens, the walls of the left ventricle (the chamber responsible for pumping blood throughout the body) do not contract simultaneously, reducing the heart's efficiency as a pump. The heart typically responds by beating faster and dilating. This results in a vicious cycle of further dilation, constriction of the vessels in the body, salt and water retention, and further worsening of heart failure. These conduction delays do not respond to antiarrhythmics or other drugs.

Patients who have heart failure may be candidates to receive a pacemaker. A biventricular pacemaker is a type of implantable pacemaker designed to treat heart failure. A biventricular pacemaker can help synchronize the lower chambers by sending electrical signals simultaneously to the left ventricle and to the right ventricle. By stimulating both ventricles (biventricular pacing), the pacemaker makes the walls of the right and left ventricles pump together again. The heart is thus resynchronized, pumping more efficiently while causing less wear and tear on the heart muscle itself. This is why biventricular pacing is also referred to as cardiac resynchronization therapy (CRT).

For patients who suffer from heart failure, remodeling of the heart may occur. Remodeling associated with heart failure is characterized by enlargement of the heart's left ventricle. In addition, the left ventricle walls become thinner. There is an increased use of oxygen, greater degree of mitral valve regurgitation, and decreased ejection fraction. Remodeling sets off a "domino effect" of further damage to heart cells and more severe heart disease. Biventricular pacing of the present invention can potentially reverse the process. This beneficial effect on the heart is called "reverse remodeling." Typical biventricular pacemakers use cathodal pulses of 2.5 volts in the atrium and 5 volts in the ventricle.

HEART ATTACK

A heart attack is an event that results in permanent heart damage or death. It is also known as a myocardial infarction, because part of the heart muscle (myocardium) may literally die (infarct). A heart attack occurs when one of the coronary arteries becomes severely or totally blocked, usually by a blood clot. When the heart muscle does not receive the oxygenated blood that it needs, it will begin to die. The severity of a heart attack usually depends on how much of the heart muscle is injured or dies during the heart attack.

Although a heart attack is usually the result of a number of chronic heart conditions (e.g., coronary artery disease), the trigger for a heart attack is often a blood clot that has blocked the flow of blood through a coronary artery. If the artery has already been narrowed by fatty plaque (a disease called atherosclerosis), the blood clot may be large enough to block the blood flow severely or completely. The victim may experience an episode of cardiac ischemia, which is a condition in which the heart is not getting enough oxygenated blood. This is often accompanied by angina (a type of chest pain, pressure or discomfort), although silent ischemia shows no signs at all. Severe or lengthy episodes of cardiac ischemia can trigger a heart attack. Depending upon the severity of both the attack and of the subsequent scarring, a heart attack can lead to the following:

Heart failure, a chronic condition in which at least one chamber of the heart is not pumping well enough to meet the body's demands.

Electrical instability of the heart, which can cause a potentially dangerous abnormal heart rhythm (arrhythmia).

Cardiac arrest, in which the heart stops beating altogether, resulting in sudden cardiac death in the absence of immediate medical attention.

Cardiogenic shock, a condition in which damaged heart muscle cannot pump normally and enters a shock-like state that is often fatal.

Death.

Whether or not the heart muscle will continue to function after a heart attack depends on how much of it was damaged or how much of it died before the patient could get medical treatment. The location of the damage in the heart muscle is also important. Because different coronary arteries supply different areas of the heart, the severity of the damage will depend upon the degree to which the artery was blocked and the amount and area of the heart muscle that depended on that blocked artery.

As previously noted, tissue that is damaged by the heart attack does not respond or responds at a slower than normal rate to excitatory pulses. The healthy tissue operates normally, but as a consequence places increased stress on this marginalized tissue, thereby "stretching" it. It is desirable to treat a heart attack so as to minimize the likelihood of continued detrimental remodeling. This can be accomplished by reducing the contraction strength of healthy cardiac tissues, by increasing the contraction strength of marginalized cardiac tissue, or by implementing a combination of both therapies.

HEART DISEASE AND ARRHYTHMIA

Disease affecting the AV junction may result in interference with normal AV conduction. This is described by different degrees of block. In first-degree block the effect is simply slowed conduction, in second-degree block there is a periodic dropped beat, but in third-degree block no signal reaches the ventricles. This latter condition is also referred to as complete heart block. In this case the ventricles are completely decoupled from the atria. Whereas the atrial heart rate is still determined at the AV node, the ventricles are paced by ectopic ventricular sites. Since under normal conditions the ventricles are driven by the atria, the latent ventricular pacemakers must have a lower rate. Consequently, in complete heart block the ventricles beat at a low rate (bradycardia). Even this condition may not require medical attention, but if the heart rate is too low, a condition known as Stokes-Adams syndrome, the situation becomes life-threatening. The prognosis in the case of complete heart block and Stokes-Adams is 50% mortality within one year. In this case the implantation of an artificial pacemaker is mandatory.

Another condition, known as the sick sinus syndrome, is also one for which the artificial pacemaker is the treatment of choice. In these conditions, the bradycardia results from the atrial rate being abnormally low. Thus, even though the AV junction is normal, the ventricles are driven at too low a rate.

A wide variety of arrhythmias can occur after acute myocardial infarction. Supraventricular tachyarrhythmias, including sinus tachycardia, atrial fibrillation, and atrial flutter, are relatively common and generally not life-threatening. Ventricular arrhythmias have a high incidence: premature ventricular beats occur in up to 90% of patients, ventricular tachycardias in up to 40% of patients, and ventricular fibrillation in up to 5%. Ventricular fibrillation is most common in the first 24 to 48 hours after myocardial infarction and is life-threatening. Although nonsustained ventricular tachycardia is of prognostic significance in the postinfarction period, it is not certain if therapy will alter prognosis. Conduction abnormalities and bradyarrhythmias, also frequent complications of acute myocardial infarction, require pacing therapy when symptomatic.

Temporary pacing is typically used first. If symptoms persist, a permanent pacemaker may be needed. A pacemaker is an artificial device to electrically assist in pacing the heart so that the heart may pump blood more effectively. Implantable electronic devices have been developed to treat both abnormally slow heart rates (bradycardias) and excessively rapid heart rates (tachycardias). The job of the pacemaker is to maintain a safe heart rate by delivering to the pumping chambers appropriately timed electrical impulses that replace the heart's normal rhythmic pulses. The device designed to perform this life-sustaining role consists of a power source the size of a silver dollar (containing the battery), and control circuits, wires or "leads" that connect the power source to the chambers of the heart. The leads are typically placed in contact with the right atrium or the right ventricle, or both. They allow the pacemaker to sense and stimulate in various combinations, depending on where the pacing is required.

Absent a diagnosis of arrhythmia, anti-arrhythmic pacing is not typically used as a treatment for myocardial infarction victims.

Whether a myocardial infarction leads to heart failure depends to a large extent on how the remaining normal heart muscle behaves. The process of ventricular dilatation (remodeling) is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation (or remodeling) of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there are both a diameter increase and a pressure increase over normal, both contributing to higher wall stress levels. The increase in diastolic wall stress is felt to be the primary contributor to ongoing dilatation of the chamber.

Inadequate pumping of blood into the arterial system by the heart is sometimes referred to as "forward failure," with "backward failure" referring to the resulting elevated pressures in the lungs and systemic veins leading to congestion. Backward failure is the natural consequence of forward failure as blood in the pulmonary and venous systems fails to be pumped out. Forward failure can be caused by impaired contractility of the ventricles or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium leading to alterations in cellular structure, a process referred to as ventricular remodeling.

Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the process ultimately results in both systolic and diastolic dysfunction. It has been shown that the extent of ventricular remodeling is positively correlated with increased mortality in CHF patients.

Over the past several years, numerous randomized clinical trials have been completed that show that two classes of drugs can significantly improve the overall survival of patients who have signs of impending heart failure (either low left ventricular ejection fraction or increased ventricular dilation). These drugs are the beta blockers and the ACE inhibitors. Beta-blockers work by blocking the effect of adrenaline on the heart, and have been noted to have numerous beneficial effects in several types of heart disease. Beta blockers reduce the risk of angina in patients with coronary artery disease, significantly improve the survival of patients with heart failure, significantly reduce the risk of sudden death in patients after heart attacks, and appear to delay or prevent the remodeling seen in the left ventricle after heart attacks. However, patients with severe asthma or other lung disease simply cannot safely take these drugs.

ACE inhibitors block angiotensin converting enzyme, and thereby produce numerous salutary effects on the cardiovascular system. This class of drugs significantly improves long-term survival among survivors of acute myocardial infarction, and in addition reduces the incidence of heart failure (apparently by preventing or delaying remodeling), recurrent heart attacks, stroke, and sudden death.

While the use of drugs may be beneficial, following a myocardial infarction the undamaged area of the heart is still required to work harder and the tissue damaged by the infarction remains unhealed.

What would be truly useful is to provide alternative methods of treating heart failure and post myocardial infarction conditions that will reduce or prevent adverse remodeling and allow damaged tissue to heal. Such alternative methods would be provided in lieu of, or in concert with, conventional pharmaceutical therapies and with new tissue-regeneration therapies.

SUMMARY

An embodiment of the present invention provides a method for treating the heart following a myocardial infarction (MI). Electrical stimulation is provided to selected portions of the heart without regard to whether a diagnosis of arrhythmia has been made. Stimulation may be in the form of excitatory or non-excitatory pulses using cathodal, anodal, and biphasic waveforms. The portions of the heart selected for stimulation are determined selected based on the type of stimulation to be administered and the extent of the damage sustained by the cardiac tissue. In an exemplary embodiment, only healthy cardiac tissue is stimulated.

In an alternative exemplary embodiment of the present invention, marginalized heart tissue can also be stimulated so that the heart beats in a more balanced fashion.

In an exemplary embodiment, biphasic, biventricular stimulation is directed to undamaged areas of the heart to enhance the muscular contraction of the healthy tissue thereby allowing the heart to achieve normal or near-normal functioning. The enhanced muscular contraction of the stimulated portion of the heart reduces uneven heart loading and prevents or reduces the adverse forms of remodeling of the heart following a myocardial infarction. The biphasic, biventricular stimulation of the exemplary embodiment of the present invention comprises continuous application of both cathodal and anodal pulses simultaneously to the right and left ventricles through electrodes that contact undamaged portions of the heart.

In an embodiment of the present invention, unlike pacing that is used to control arrhythmias, the non-excitatory biphasic stimulation is not applied to the heart in response to sensing a cardiac signal indicative of an arrhythmia. Rather, the non-excitatory biphasic stimulation is applied continuously to allow the heart to compensate for the cardiac tissue affected by a MI while avoiding undesirable forms of remodeling. Optionally, the application of the biphasic stimulation is timed to coincide with an initialization of a depolarization wave as determined by cardiac sensors.

Additionally, the stimulation of the exemplary embodiment may be combined with stem cell implantation at sites where the cardiac tissue has been damaged. The stem cell therapy regenerates damaged cardiac tissue so that over time, the stimulation therapy may be terminated.

In this exemplary embodiment of the present invention, the prevention of adverse remodeling stems from a number of mechanisms. The effect of bi-ventricular pacing provides increased inotropic effect while at the same time reducing oxygen demand and consumption by the heart, and by reducing and equalizing the wall tension, in effect reducing the tendency to stretch damaged areas of the heart. Also, the stimulus for stem cell implantation and proper orientation depends on proper wall tension and electrical activity over the damaged area. These conditions are properly established by this treatment. Additionally, the exposure of the damaged cardiac tissue to an electrical current can directly heal damaged areas. This is similar to the use of currents of proper polarity to heal other tissues such as fractures of bone and skin incisions.

As will be appreciated by those skilled in the art, the description of exemplary embodiments is not limiting. While biphasic, bi-ventricular stimulation is described herein, other waveforms and stimulation sites may be employed to reduce the workload on the undamaged cardiac tissue and to thereby allow the heart to reverse or avoid the undesirable remodeling. Additionally, therapies may utilize excitatory or non-excitatory pulses. As previously noted, tissue that is damaged by the heart attack does not respond or responds at a slower than normal rate to excitatory pulses. The healthy tissue places increased stress on this marginalized tissue, thereby "stretching" it. It is desirable to treat a heart attack so as to minimize the likelihood of continued detrimental remodeling. This can be accomplished by reducing the contraction strength of healthy cardiac tissues, by increasing the contraction strength of marginalized cardiac tissue, or by implementing a combination of both therapies.

It is therefore an aspect of the present invention to promote the healing of cardiac tissue affected by a MI.

It is another aspect of the present invention to increase cardiac output of cardiac tissue not affected by a MI through more coordinated cardiac contraction leading to greater stroke volume with less cardiac work required.

It is yet another aspect of the present invention to stimulate marginalized areas of cardiac tissue so that they contract to some extent leading to more balanced operation of the heart post-MI.

It is still another aspect of the present invention to apply a combination of stimulation to tissue that is damaged and to tissue that is undamaged by an MI to promote balanced functioning of cardiac tissue post-MI.

It is still another aspect of the present invention to reduce the adverse forms of remodeling of the heart following an MI.

It is yet another aspect of the present invention to continuously stimulate selection portions of the heart not affected by an MI using stimulation pulses.

It is a further aspect of the present invention to promote the healing of cardiac tissue affected by a MI using stem cells.

It is another aspect of the present invention to maintain wall tension in the heart at acceptable levels in patients suffering from heart disease.

It is a further aspect of the present invention to promote normalizing of wall stresses thereby promoting the implantation of stem cells in damaged tissue.

These and other aspects of the present invention will be apparent from the general and detailed description that follows.

According to an embodiment of the present invention, an apparatus for minimizing cardiac remodeling of a non-arrhythmic patient comprises a heart stimulation device, a left ventricular electrode group, and a right ventricular electrode group. The left ventricular electrode group comprises LV electrodes attached to the left ventricle at increasing distances from the AV node. The right ventricular electrode group comprises RV electrodes attached to the left ventricle at increasing distances from the AV node. The heart stimulation device is adapted to stimulate healthy and compromised areas of cardiac tissue.

The heart stimulation device attaches to the LV and RV electrodes and generates a timing signal coincident with a refractory period. In response to the timing signal, the heart stimulation device sends pulses to the LV and RV electrodes sequenced such that an initial pulse arrives at an LV electrode and at an RV electrode nearest the AV junction and subsequent pulses arrive at an LR and at an RV electrode progressively further from the AV junction.

In an embodiment of the present invention, the pulse is excitatory. In another embodiment of the present invention, the pulse is non-excitatory. In yet another embodiment of the present invention, the pulse is biphaisic.

According to an embodiment of the present invention, the biphasic pulse comprises a first stimulation phase having a first phase polarity, a first phase amplitude, a first phase shape, and a first phase duration, so as to precondition the myocardium to accept subsequent stimulation. The biphasic pulse further comprises a second stimulation phase having a second phase polarity, as second phase amplitude that is larger in absolute value than the first phase amplitude, a second phase shape, and a second phase duration. In an embodiment of the present invention, the first phase polarity is positive, and the second phase polarity is negative. In yet another embodiment of the present invention, the first phase amplitude is at a maximum subthreshold amplitude.

In an embodiment of the present invention, stem cells are deposited on the cardiac tissue. In one embodiment of the present invention, the LV and RV electrodes are located so as to electrically stimulate the compromised area of cardiac tissue on which stem cells have been deposited. In an alternate embodiment of the present invention, the LV and RV electrodes are located so as to preclude electrical stimulation of the compromised area of cardiac tissue on which stem cells have been deposited.

According to an embodiment of the present invention, an apparatus for minimizing cardiac remodeling of a non-arrhythmic patient comprises a heart stimulation device, a left ventricular electrode group, a right ventricular electrode group, and a sensor. The sensor senses excitation of a heart chamber.

The left ventricular electrode group comprises LV electrodes attached to the left ventricle at increasing distances from the AV node. The right ventricular electrode group comprises RV electrodes attached to the left ventricle at increasing distances from the AV node. The heart stimulation device is adapted to stimulate healthy and compromised areas of cardiac tissue.

The heart stimulation device attaches to the LV and RV electrodes and the sensor. In response to a signal from the sensor, the heart stimulation device sends pulses to the LV and RV electrodes sequenced such that an initial pulse arrives at an LV electrode and at an RV electrode nearest the AV junction and subsequent pulses arrive at an LR and at an RV electrode progressively further from the AV junction.

In an embodiment of the present invention, the pulse is excitatory. In another embodiment of the present invention, the pulse is non-excitatory. In yet another embodiment of the present invention, the pulse is biphaisic.

According to an embodiment of the present invention, the biphasic pulse comprises a first stimulation phase having a first phase polarity, a first phase amplitude, a first phase shape, and a first phase duration, so as to precondition the myocardium to accept subsequent stimulation. The biphasic pulse further comprises a second stimulation phase having a second phase polarity, a second phase amplitude that is larger in absolute value than the first phase amplitude, a second phase shape, and a second phase duration. In an embodiment of the present invention, the first phase polarity is positive, and the second phase polarity is negative. In yet another embodiment of the present invention, the first phase amplitude is at a maximum subthreshold amplitude.

In an embodiment of the present invention, stem cells are deposited on the cardiac tissue. In one embodiment of the present invention, the LV and RV electrodes are located so as to electrically stimulate the compromised area of cardiac tissue on which stem cells have been deposited. In an alternate embodiment of the present invention, the LV and RV electrodes are located so as to preclude electrical stimulation of the compromised area of cardiac tissue on which stem cells have been deposited.

An embodiment of the present invention provides a method for minimizing cardiac remodeling of a non-arrhythmic patient. Stem cells are administered to a myocardial infarct (MI) area of a patient. Biphasic bi-ventricular stimulation is continuously administered to cardiac tissue outside of the MI area.

According to an embodiment of the present invention, the biphasic pulse comprises a first stimulation phase having a first phase polarity, a first phase amplitude, a first phase shape, and a first phase duration, so as to precondition the myocardium to accept subsequent stimulation. The biphasic pulse further comprises a second stimulation phase having a second phase polarity, a second phase amplitude that is larger in absolute value than the first phase amplitude, a second phase shape, and a second phase duration. In an embodiment of the present invention, the first phase polarity is positive, and the second phase polarity is negative. In yet another embodiment of the present invention, the first phase amplitude is at a maximum subthreshold amplitude.

In an embodiment of the present invention, stem cells are deposited on the cardiac tissue. In one embodiment of the present invention, the LV and RV electrodes are located so as to electrically stimulate the compromised area of cardiac tissue on which stem cells have been deposited. In an alternate embodiment of the present invention, the LV and RV electrodes are located so as to preclude electrical stimulation of the compromised area of cardiac tissue on which stem cells have been deposited.

According to an embodiment of the present invention, an apparatus for minimizing cardiac remodeling of a non-arrhythmic patient comprises a heart stimulation device, a left ventricular electrode group, a right ventricular electrode group, and a sensor. The sensor senses excitation of a heart chamber.

The left ventricular electrode group comprises LV electrodes attached to the left ventricle at increasing distances from the AV node. The right ventricular electrode group comprises RV electrodes attached to the left ventricle at increasing distances from the AV node. The heart stimulation device is adapted to stimulate healthy and compromised areas of cardiac tissue. A compromised area of the heart has stem cells deposited thereon.

The heart stimulation device attaches to the LV and RV electrodes and the sensor. In response to a signal from the sensor, the heart stimulation device sends pulses to the LV and RV electrodes sequenced such that an initial pulse arrives at an LV electrode and at an RV electrode nearest the AV junction and subsequent pulses arrive at an LV and at an RV electrode progressively further from the AV junction.

In an embodiment of the present invention, stem cells are deposited on the cardiac tissue. In one embodiment of the present invention, the LV and RV electrodes are located so as to electrically stimulate the compromised area of cardiac tissue on which stem cells have been deposited. In an alternate embodiment of the present invention, the LV and RV electrodes are located so as to preclude electrical stimulation of the compromised area of cardiac tissue on which stem cells have been deposited.

DETAILED DESCRIPTION

An embodiment of the present invention provides a method for treating the heart following a myocardial infarction (MI).

Electrical stimulation is provided to selected portions of the heart without regard to whether a diagnosis of any arrhythmia has been given. Stimulation may be in the form of excitatory or non-excitatory pulses using cathodal, anodal, and biphasic waveforms. The portions of the heart selected for stimulation are selected based on the type of stimulation to be administered and the extent of the damage sustained by the cardiac tissue. In an exemplary embodiment, only healthy cardiac tissue is stimulated.

In an exemplary embodiment of the present invention, biphasic, biventricular stimulation is directed to undamaged areas of the heart to enhance the muscular contraction of the healthy tissue thereby allowing the heart to achieve normal or near-normal functioning. The enhanced muscular contraction of the stimulated portion of the heart reduces heart loading and prevents or reduces the adverse forms of remodeling of the heart following a myocardial infarction. The biphasic, biventricular stimulation comprises continuous application of both cathodal and anodal pulses simultaneously to the right and left ventricles through electrodes that contact undamaged portions of the heart.

In an embodiment of the present invention, unlike pacing that is used to control arrhythmias, the biphasic stimulation is not applied to the heart in response to sensing a cardiac signal indicative of an arrhythmia. Rather, the biphasic stimulation is applied continuously to allow the heart to compensate for the cardiac tissue affected by an MI while avoiding undesirable forms of remodeling. Optionally, the application of the biphasic stimulation is timed to coincide with the beginning of a depolarization wave as determined by cardiac sensors.

Additionally, the biphasic stimulation of the exemplary embodiment is combined with stem cell implantation at sites where the cardiac tissue has been damaged. The stem cell therapy regenerates damaged cardiac tissue so that over time, the biphasic stimulation therapy may be terminated.

Figure 1:
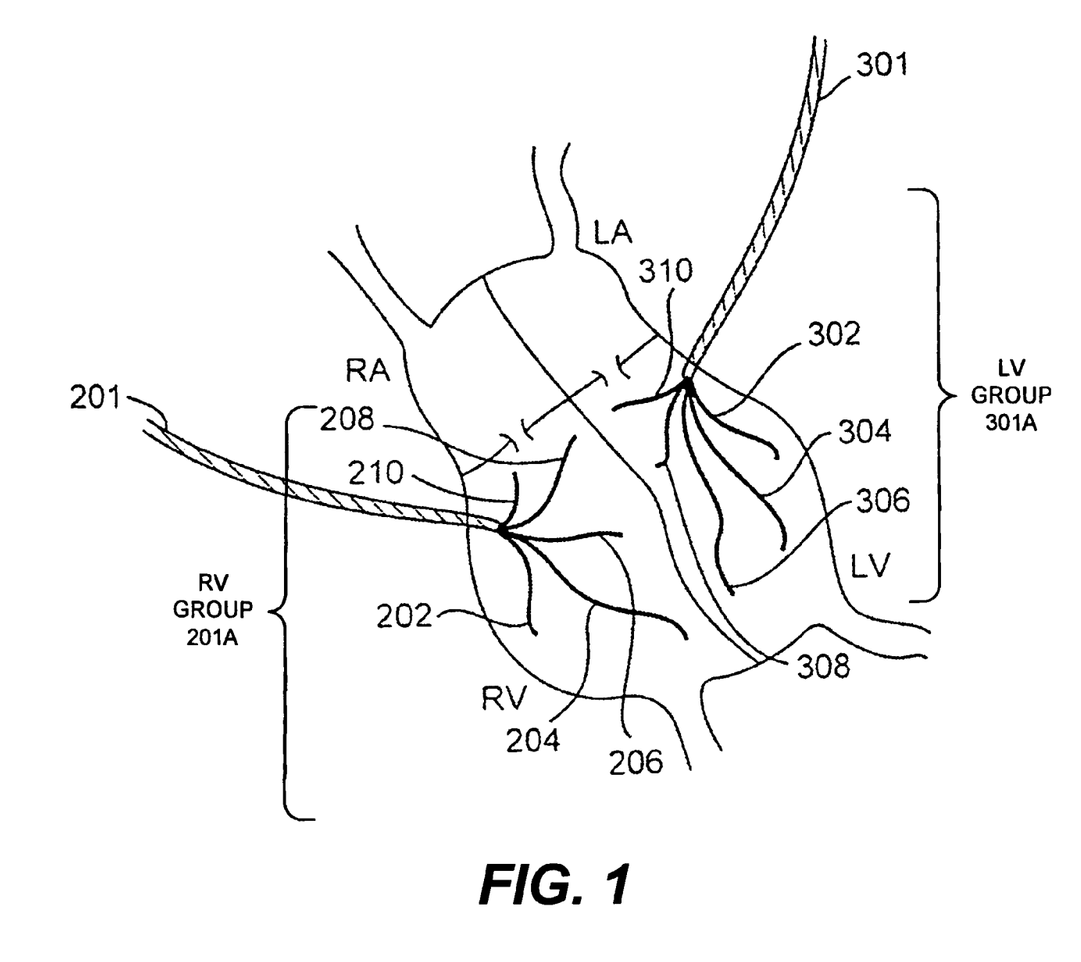
FIG. 1 illustrates a heart with multiple ventricular electrodes that are connected to external surfaces of the ventricles, and includes a separate electrode set for each of the right and left ventricles according to embodiments of the present invention.

Referring to FIG. 1, a diagram of the heart illustrates the four chambers: right atrium (RA), left atrium (LA), right ventricle (RV), and left ventricle (LV). Electrode lead 201, connected to RV electrode group 201A comprising individual electrodes 202, 204, 206, 208 and 210, is shown with the individual electrodes connected to multiple points on the external surfaces of the right ventricle. Electrode lead 301, connected to LV electrode group 301A comprising individual electrodes 302, 304, 306, 308 and 310, is shown with the individual electrodes connected to multiple points on the external surfaces of the left ventricle. While RV electrode group 201A and LV electrode group 301A are illustrated with five electrodes per group, this is not meant as a limitation. Other group sizes may be used without departing from the scope of the present invention.

In alternative embodiments, the locations of the individual electrodes in FIG. 1 (202, 204, 206, 208 and 210; and 302, 304, 306, 308 and 310) are selected to avoid stimulation of damaged cardiac tissue as, for example, tissue damaged as a result of an MI.

In yet another embodiment of the present invention, pulses are applied to the electrodes so as to mimic the normal physiological flow of the normal ventricular depolarization wave. In this embodiment, the areas closest to (or at) the A-V node are first stimulated during a given beat. In an embodiment of the present invention, atrial excitation is sensed (P-Q interval) or ventricular excitation is sensed (QRS interval) and an external excitatory pulse is applied to the first electrode (after an appropriate delay) to coincide with the beginning of the ventricular depolarization wave. Subsequent excitatory pulses are directed to areas progressively further from the A-V node. Areas intermediate between these two extremes are appropriately stimulated on a scaled time basis that, again, mimics the normal intrinsic conduction paths that facilitate the most efficient cardiac contraction. In an embodiment of the present invention, the pulses are applied to healthy cardiac tissue that is unaffected by the MI, thereby allowing the damaged tissue to heal and the stimulation voltage to be low.

This progressive stimulation embodiment requires specific knowledge of the placement of each electrode relative to each other electrode, as well as the placement relative to the electrical conduction pathways in the heart. Thus, it is appropriate to contemplate "classes" of electrodes, in which, for example, electrodes are identified or categorized according to when they are fired. In a simplistic five tier system, e.g., the first tier electrodes are designated as the first to be fired (i.e., the electrodes closest to the A-V node), followed successively (and temporally progressively according to the normal conducting paths) by the second, third, fourth, and fifth tier electrodes, where the fifth tier electrodes would be the last to be fired, and whose locations on the ventricle(s) would correspond to the last areas to be depolarized in the course of a normal ventricular contraction/beat. An even simpler (i.e., two, three or four) tiered system may be used, or one more complex (i.e., one with greater than five tiers, or with any other basis of electrode placement, such as a honeycomb-like array in a particular area with a known or suspected pathology as to rhythmicity, reentry, conduction, contractility, etc. Furthermore, multiple electrodes within a given tier may be numbered or otherwise distinctly identified so that the practitioner may test and use electrodes with respect to known locations in the heart, for example, to anticipate and/or bypass an area of electrical blockage. In this embodiment, multiple, small electrodes are pulsed with excitatory pulses in a physiologic sequential fashion.

In still another embodiment of the present invention, the technique described above for stimulating the ventricles is applied to the atria. In this embodiment, electrodes are progressively placed from close to the SA node (first to be fired) to close to the AV node (last to be fired), mimicking the normal intrinsic conduction paths of the atria.

Bypassing an area of damaged tissue is also anticipated by the present invention, and can be effected by first identifying such areas, for example, by determining myocardial resistance values between electrodes. Electrical pulses then are routed to those myocardial areas with appropriately low resistances, following as closely as possible the lines of conduction of the normal intrinsic conduction paths. Communication of, and control of, measurements of resistance between electrodes, as well as developing a bypass protocol for a particular patient, can be effected by an external computer. The external computer can communicate with the pacemaker by any convenient method, for example, radiotelemetry, direct coupling (as by connecting to an external wire from the pacemaker to the surface of the skin of the patient), etc.

FIGS. 2 through 5 depict a range of biphasic stimulation protocols. These protocols have been disclosed in U.S. Pat. No. 5,871,506 to Mower, which is herein incorporated by reference in its entirety.

Figure 2:
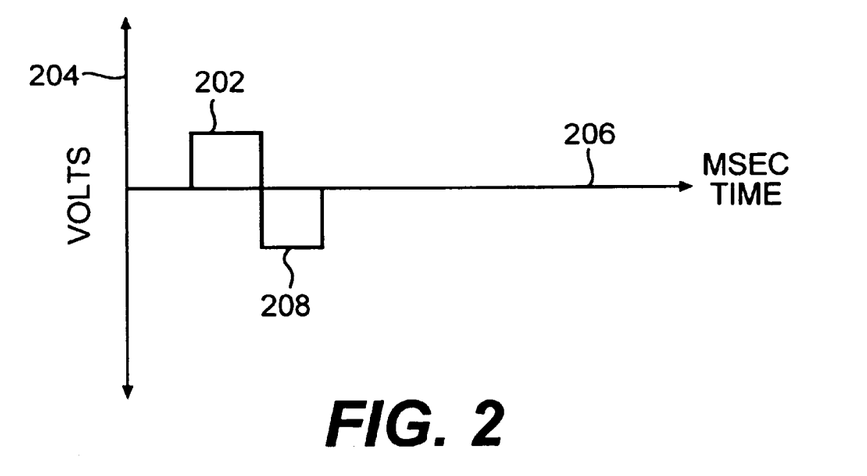
FIG. 2 is a schematic representation of a leading anodal biphasic stimulation according to an embodiment of the present invention.

FIG. 2 depicts biphasic electrical stimulation in which a first stimulation phase comprising anodal stimulus 202 is administered with amplitude 204 and duration 206. The first stimulation phase is followed immediately by a second stimulation phase comprising cathodal stimulus 208, which is of equal intensity and duration to those of anodal stimulus 202.

Figure 3:
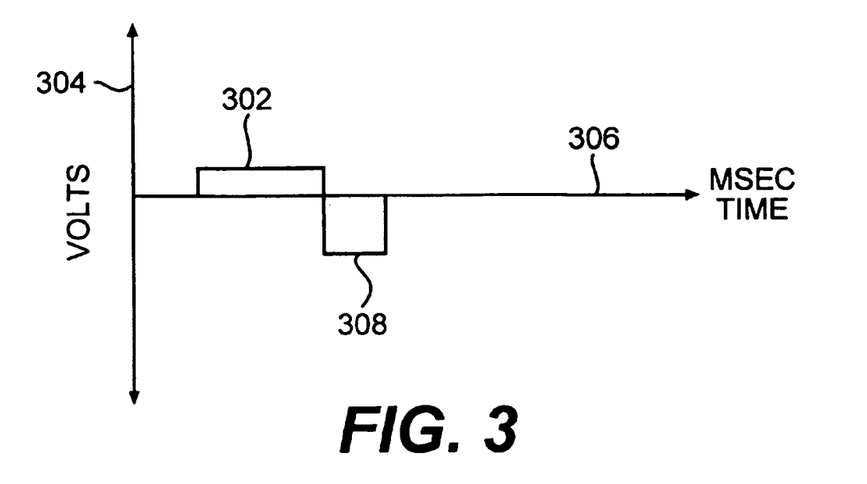
FIG. 3 is a schematic representation of a leading anodal stimulation of low level and long duration, followed by cathodal stimulation according to an embodiment of the present invention.

FIG. 3 depicts biphasic electrical stimulation wherein a first stimulation phase comprising low level, long duration anodal stimulation 302 having amplitude 304 and duration 306 is administered. This first stimulation phase is immediately followed by a second stimulation phase comprising cathodal stimulation 308 of conventional intensity and duration. In an alternative embodiment of the invention, anodal stimulation 302 is at maximum subthreshold amplitude. In yet another alternative embodiment of the invention, anodal stimulation 302 is less than three volts. In another alternative embodiment of the invention, anodal stimulation 302 is a duration of approximately two to eight milliseconds. In yet another alternative embodiment of the invention, cathodal stimulation 308 is of a short duration. In another alternative embodiment of the invention, cathodal stimulation 308 is approximately 0.3 to 1.5 milliseconds. In yet another alternative embodiment of the invention, cathodal stimulation 308 is of a high amplitude. In another alternative embodiment of the invention, cathodal stimulation 308 is in the approximate range of three to twenty volts. In yet another alternative embodiment of the present invention, cathodal stimulation 308 is of a duration less than 0.3 milliseconds and at a voltage greater than twenty volts. In another alternative embodiment, anodal stimulation 302 is administered over 200 milliseconds post heart beat. In the manner disclosed by these embodiments, as well as those alterations and modifications which may become obvious upon the reading of this specification, a maximum membrane potential without activation is achieved in the first phase of stimulation.

Figure 4:
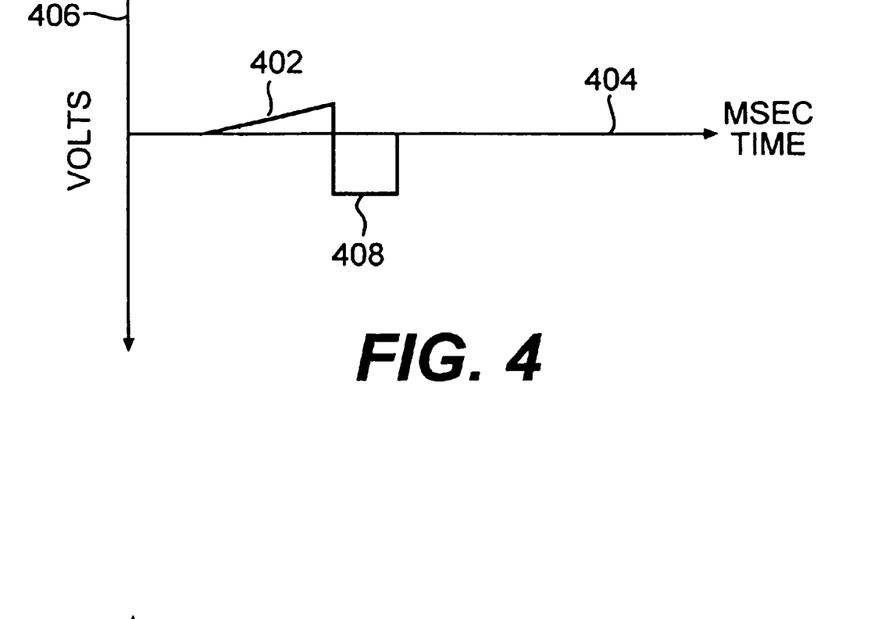
FIG. 4 is a schematic representation of leading anodal stimulation of ramped low level and long duration, followed by cathodal stimulation according to an embodiment of the present invention.

FIG. 4 depicts biphasic electrical stimulation wherein a first stimulation phase comprising anodal stimulation 402 is administered over period 404 with rising intensity level 406. The ramp of rising intensity level 406 may be linear or non-linear, and the slope may vary. This anodal stimulation is immediately followed by a second stimulation phase comprising cathodal stimulation 408 of conventional intensity and duration. In an alternative embodiment of the invention, anodal stimulation 402 rises to a maximum subthreshold amplitude. In yet another alternative embodiment of the invention, anodal stimulation 402 rises to a maximum amplitude that is less than three volts. In another alternative embodiment of the invention, anodal stimulation 402 is of a duration of approximately two to eight milliseconds. In yet another alternative embodiment of the invention, cathodal stimulation 408 is of a short duration. In another alternative embodiment of the invention, cathodal stimulation 408 is approximately 0.3 to 1.5 milliseconds. In yet another alternative embodiment of the invention, cathodal stimulation 408 is of a high amplitude. In another alternative embodiment of the invention, cathodal stimulation 408 is in the approximate range of three to twenty volts. In yet another alternative embodiment of the present invention, cathodal stimulation 408 is of a duration less than 0.3 milliseconds and at a voltage greater than twenty volts. In another alternative embodiment, anodal stimulation 402 is administered over 200 milliseconds post heart beat. In the manner disclosed by these embodiments as well as those alterations and modifications which may become obvious upon the reading of this specification, a maximum membrane potential without activation is achieved in the first phase of stimulation.

Figure 5:
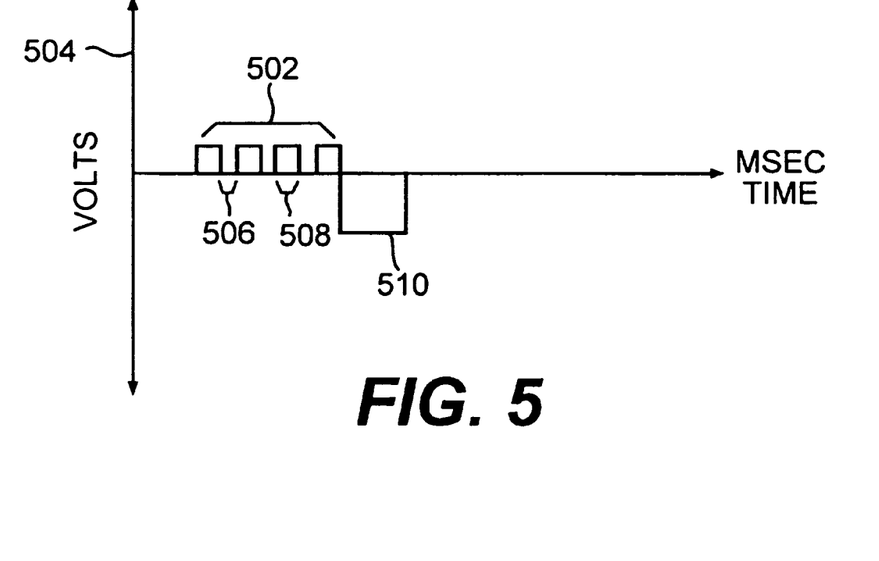
FIG. 5 is a schematic representation of leading anodal stimulation of low level and short duration administered in a series, followed by cathodal stimulation according to an embodiment of the present invention.

FIG. 5 depicts biphasic electrical stimulation wherein a first stimulation phase comprising series 502 of anodal pulses is administered at amplitude 504. In one embodiment rest period 506 is of equal duration to stimulation period 508 and is administered at baseline amplitude. In an alternative embodiment, rest period 506 is of a differing duration than stimulation period 508 and is administered at baseline amplitude. Rest period 506 occurs after each stimulation period 508 with the exception that a second stimulation phase comprising cathodal stimulation 510 of conventional intensity and duration immediately follows the completion of series 502. In an alternative embodiment of the invention, the total charge transferred through series 502 of anodal stimulation is at the maximum subthreshold level. In yet another alternative embodiment of the invention, the first stimulation pulse of series 502 is administered over 200 milliseconds post heart beat. In another alternative embodiment of the invention, cathodal stimulation 510 is of a short duration. In yet another alternative embodiment of the invention, cathodal stimulation 510 is approximately 0.3 to 1.5 milliseconds. In another alternative embodiment of the invention, cathodal stimulation 510 is of a high amplitude. In yet another alternative embodiment of the invention, cathodal stimulation 510 is in the approximate range of three to twenty volts. In another alternative embodiment of the invention, cathodal stimulation 510 is of a duration less than 0.3 milliseconds and at a voltage greater than twenty volts. The individual pulses of the series of pulses may be square waves, or they may be of any other shape, for example, pulses which decay linearly or curvilinearly from an initial subthreshold amplitude, to a lower amplitude.

In the biphasic stimulation protocol practiced by the present invention, the magnitude of the anodal phase does not exceed the maximum subthreshold amplitude. The anodal phase serves to precondition the stimulated myocardium, thereby lowering the excitation threshold such that a cathodal stimulation of lesser intensity than normal will produce depolarization leading to contraction.

The pacing and subsequent normalizing of wall stresses promotes the implantation of stem cells in damaged tissue, and guides their proper orientation during the maturation of the cells.

The values of duration and amplitude will depend on factors such as the placement/position of the particular electrode (including, e.g., whether the electrode is in purely muscle tissue versus in specialized conducting or pacemaking tissue), whether damaged/scarred tissue is in close vicinity to the electrode, depth of the electrode within the tissue, local tissue resistance, presence or absence of any of a large range of local pathologies, etc. Nonetheless, typical anodal phase durations often fall within the range from about two milliseconds to about eight milliseconds, whereas typical cathodal durations often fall within the range from about 0.3 milliseconds to about 1.5 milliseconds. Typical anodal phase amplitudes (most commonly at the maximum subthreshold amplitude) often fall within the range from about 0.5 volt to 3.5 volts, compared to typical cathodal phase amplitudes from about 3 volts to about 20 volts.

Because the heart is constantly stimulated, the pacing pulses are applied without the need for demand sensing. Further, constant consistent pacing diminishes stress on the heart.

In another embodiment of the present invention, the damaged tissue is located and treated by inserting or applying donor or "stem" cells. Means for inserting and means for applying stem cells to damaged cardiac tissue are described in U.S. Patent Application No. 60/429,954, entitled "Method and Apparatus for Cell and Electrical Therapy of Living Tissue," a utility application for which was filed on Nov. 25, 2003, both of which applications are incorporated herein in their entirety for all purposes. In an embodiment of the present invention, the damaged tissue is treated and biventricular pacing pulsing is continuously applied to functioning portions of the heart. In one embodiment, the pacing sites are chosen to assure that the tissue treated with stem cells is not electrically stimulated. In an alternate embodiment, the pacing sites are chosen so that the tissue treated with stem cells receives electrical stimulation pulses having an amplitude below that required to excite the heart tissue.

A system and method for managing detrimental cardiac remodeling following myocardial infarction have been disclosed. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the," is not to be construed as limiting the element to the singular.

What is claimed is:

1. An apparatus for minimizing cardiac remodeling of a non-arrhythmic patient comprising:
    a heart stimulation device comprising control circuitry, wherein the control circuitry is configured with instructions for stimulating cardiac tissue, wherein the cardiac tissue comprises healthy and compromised areas;
    a left ventricular electrode group, wherein the left ventricular electrode group comprises LV electrodes attached to the left ventricle at increasing distances from the AV node; and
    a right ventricular electrode group, wherein the right ventricular electrode group comprises RV electrodes attached to the left ventricle at increasing distances from the AV node,
    wherein the heart stimulation device is configured to attach to the LV and RV electrodes, and wherein instructions for stimulating cardiac tissue include instructions configured to cause the control circuitry to perform operations comprising:
        generating a timing signal coincident with a refractory period: and
        in response to the timing signal, sending a series of biphasic pulses to the LV and RV electrodes, wherein the series of biphasic pulses is sequenced such that an initial pulse arrives at an LV electrode and an RV electrode nearest the AV junction, and subsequent pulses arrive at an LV and an RV electrode progressively further from the AV junction.

2. The apparatus for minimizing cardiac remodeling of a non-arrhythmic patient of claim 1, wherein at least one of the biphasic pulses in the series of biphasic pulses is excitatory.

3. The apparatus for minimizing cardiac remodeling of a non-arrhythmic patient of claim 1, wherein at least one of the biphasic pulses in the series of biphasic pulses is non-excitatory.

4. The apparatus for minimizing cardiac remodeling of a non-arrhythmic patient of claim 1, wherein each one of the biphasic pulses in the series of biphasic pulses comprises:
    a first stimulation phase having a first phase polarity, a first phase amplitude, a first phase shape, and a first phase duration, so as to precondition the myocardium to accept subsequent stimulation, and
    a second stimulation phase having a second phase polarity, a second phase amplitude that is larger in absolute value than the first phase amplitude, a second phase shape, and a second phase duration.

5. The apparatus for minimizing cardiac remodeling of a non-arrhythmic patient according to claim 4, wherein the first phase polarity is positive, and the second phase polarity is negative.

6. The apparatus for minimizing cardiac remodeling of a non-arrhythmic patient according to claim 4, wherein the first phase amplitude is at a maximum subthreshold amplitude.

7. The apparatus for minimizing cardiac remodeling of a non-arrhythmic patient according to claim 1, wherein a compromised area of cardiac tissue has stem cells deposited thereon.

8. The apparatus for minimizing cardiac remodeling of a non-arrhythmic patient according to claim 7, wherein the LV and RV electrodes are located so as to electrically stimulate the compromised area of cardiac tissue on which stem cells have been deposited.

9. The apparatus for minimizing cardiac remodeling of a non-arrhythmic patient according to claim 7, wherein the LV and RV electrodes are located so as to preclude electrical stimulation of the compromised area of cardiac tissue on which stem cells have been deposited.

10. An apparatus for minimizing cardiac remodeling of a non-arrhythmic patient comprising:
    a heart stimulation device comprising control circuitry, wherein the control circuitry is configured with instructions for stimulating cardiac tissue, wherein the cardiac tissue comprises healthy and compromised areas;
    a left ventricular electrode group, wherein the left ventricular electrode group comprises LV electrodes attached to the left ventricle at increasing distances from the AV node;
    a right ventricular electrode group, wherein the right ventricular electrode group comprises RV electrodes attached to the left ventricle at increasing distances from the AV node; and
    a sensor configured to sense excitation of a heart chamber, wherein the heart stimulation device is configured to attach to the LV and RV electrodes and to the sensor, and wherein the instructions for stimulating cardiac tissue include instructions configured to cause the control circuitry to perform operations comprising:
        in response to a signal from the sensor, sending a series of biphasic pulses to the LV and RV electrodes, wherein the series of biphasic pulses is sequenced such that an initial pulse arrives at an LV electrode and an RV electrode nearest the AV junction and subsequent pulses arrive at an LV and an RV electrode progressively further from the AV junction.

11. The apparatus for minimizing cardiac remodeling of a non-arrhythmic patient of claim 10, wherein at least one of the biphasic pulses in the series of biphasic pulses is excitatory.

12. The apparatus for minimizing cardiac remodeling of a non-arrhythmic patient of claim 10, wherein at least one of the biphasic pulses in the series of biphasic pulses is non-excitatory.

13. The apparatus for minimizing cardiac remodeling of a non-arrhythmic patient of claim 10, wherein each of the biphasic pulses in the series of biphasic pulses comprises:
    a first stimulation phase having a first phase polarity, a first phase amplitude, a first phase shape, and a first phase duration, so as to precondition the myocardium to accept subsequent stimulation, and
    a second stimulation phase having a second phase polarity, a second phase amplitude that is larger in absolute value than the first phase amplitude, a second phase shape, and a second phase duration.

14. The apparatus for minimizing cardiac remodeling of a non-arrhythmic patient according to claim 13, wherein the first phase polarity is positive, and the second phase polarity is negative.

15. The apparatus for minimizing cardiac remodeling of a non-arrhythmic patient according to claim 13, wherein the first phase amplitude is at a maximum subthreshold amplitude.

16. The apparatus for minimizing cardiac remodeling of a non-arrhythmic patient according to claim 10, wherein a compromised area of cardiac tissue has stem cells deposited thereon.

17. The apparatus for minimizing cardiac remodeling of a non-arrhythmic patient according to claim 16, wherein the LV and RV electrodes are located so as to electrically stimulate the compromised area of cardiac tissue on which stem cells have been deposited.

18. The apparatus for minimizing cardiac remodeling of a non-arrhythmic patient according to claim 16, wherein the LV and RV electrodes are located so as to preclude electrical stimulation of the compromised area of cardiac tissue on which stem cells have been deposited.

19. An apparatus for minimizing cardiac remodeling of a non-arrhythmic patient comprising:
- a heart stimulation device comprising control circuitry, wherein the control circuitry is configured with instructions for stimulating cardiac tissue, wherein the cardiac tissue comprises:
  - a healthy area; and
  - a compromised area that has stem cells deposited thereon;
- a left ventricular electrode group, wherein the left ventricular electrode group comprises LV electrodes attached to the left ventricle at increasing distances from the AV node;
- a right ventricular electrode group, wherein the right ventricular electrode group comprises RV electrodes attached to the left ventricle at increasing distances from the AV node; and
- a sensor configured to sense excitation of a heart chamber, wherein the heart stimulation device is configured to attach to the LV and RV electrodes and to the sensor, and wherein instructions for stimulating cardiac tissue include instructions configured to cause the control circuitry to perform operations comprising:
  - in response to a signal from the sensor, sending biphasic stimulation to the LV and RV electrodes, wherein the series of biphasic pulses is sequenced such that an initial pulse arrives at an LV electrode and an RV electrode nearest the AV junction, and subsequent pulses arrive at an LV and an RV electrode progressively further from the AV junction; and
  - wherein the biphasic stimulation comprises:
    - a first stimulation phase having a first phase polarity, a first phase amplitude, a first phase shape, and a first phase duration, so as to precondition the myocardium to accept subsequent stimulation, and
    - a second stimulation phase having a second phase polarity, a second phase amplitude that is larger in absolute value than the first phase amplitude, a second phase shape, and a second phase duration.

20. The apparatus for minimizing cardiac remodeling of a non-arrhythmic patient according to claim 19, wherein the LV and RV electrodes are located so as to electrically stimulate the compromised area of cardiac tissue on which stem cells have been deposited.

21. The apparatus for minimizing cardiac remodeling of a non-arrhythmic patient according to claim 19, wherein the LV and RV electrodes are located so as to preclude electrical stimulation of the compromised area of cardiac tissue on which stem cells have been deposited.

* * * * *